United States Patent
Nguyen et al.

(10) Patent No.: US 6,748,634 B2
(45) Date of Patent: Jun. 15, 2004

(54) TAMPON HAVING IMPROVED EARLY EXPANSION CHARACTERISTICS

(75) Inventors: Hien Nguyen, East Windsor, NJ (US); Nicolas Martens, Wuppertal (DE); Glenn Garbolino, Edison, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 51 days.

(21) Appl. No.: 10/161,860

(22) Filed: Jun. 4, 2002

(65) Prior Publication Data
US 2003/0055391 A1 Mar. 20, 2003

Related U.S. Application Data

(62) Division of application No. 08/557,568, filed on Dec. 22, 1995, now Pat. No. 5,907,666.

(51) Int. Cl.$^7$ .................................................. A61F 13/20
(52) U.S. Cl. ............................................. 28/118; 28/121
(58) Field of Search .................... 28/118, 119, 120, 28/121; 604/358, 375, 384, 385.18, 367, 374, 378, 379, 380, 904

(56) References Cited

U.S. PATENT DOCUMENTS

| | | | | |
|---|---|---|---|---|
| 3,340,874 A | * | 9/1967 | Burgeni | 604/379 |
| 3,976,075 A | * | 8/1976 | Chinai et al. | 128/285 |
| 4,041,948 A | * | 8/1977 | Flam et al. | 128/285 |
| 4,129,679 A | * | 12/1978 | Woodings | 428/398 |
| 4,217,901 A | * | 8/1980 | Bradstreet et al. | 128/290 R |
| 4,239,043 A | * | 12/1980 | Gellert | 128/285 |
| 4,341,214 A | * | 7/1982 | Fries et al. | 128/285 |
| 4,475,911 A | * | 10/1984 | Gellert | 604/367 |
| 4,627,849 A | * | 12/1986 | Walton et al. | 604/379 |
| 4,816,100 A | * | 3/1989 | Friese | 156/191 |
| 5,165,152 A | * | 11/1992 | Kramer et al. | 28/118 |
| 5,458,835 A | * | 10/1995 | Wilkes et al. | 264/143 |
| 5,592,725 A | * | 1/1997 | Brinker | 28/118 |
| 5,634,914 A | * | 6/1997 | Wilkes et al. | 604/375 |
| 5,750,446 A | * | 5/1998 | Nguyen et al. | 442/337 |
| 6,310,269 B1 | * | 10/2001 | Friese et al. | 604/379 |

FOREIGN PATENT DOCUMENTS

| | | | |
|---|---|---|---|
| EP | 301874 | * | 2/1989 |
| EP | 301874 B1 | * | 6/1992 |
| EP | 716170 A2 | * | 12/1994 |
| WO | WO 89/01062 | * | 2/1989 |

* cited by examiner

*Primary Examiner*—A. Vanatta

(57) ABSTRACT

A tampon formed of a substantially cylindrical mass of compressed fibers substantially enclosed in a fluid-permeable cover has improved ability to prevent early leakage. This tampon has a stability of at least about 15 N, and is capable of radially expanding upon exposure to a humid environment. The radius increases by at least about 10% after 15 minutes to 90% relative humidity at 40° C.

4 Claims, 1 Drawing Sheet

TAMPON HAVING IMPROVED EARLY EXPANSION CHARACTERISTICS

This application is a divisional application related to the following application: U.S. Ser. No. 08/557,568 filed on Dec. 22, 1995, now U.S. Pat. No. 5,907,666.

FIELD OF THE INVENTION

The present invention relates to a compressed, radially-expanding, generally cylindrical, fibrous tampon. These tampons rapidly expand in environments of high humidity and provide improved early expansion characteristics.

BACKGROUND OF THE INVENTION

Catamenial tampons are used to absorb, not block the flow of, menstrual fluids to prevent leakage, for example, staining of a user's garments. Unfortunately, commercial tampons are subject to two major types of failure: a tampon's inability to continue to absorb fluids once the absorption capacity of the tampon is reached, and a tampon's inability to immediately expand to fill the vaginal cavity. Thus, until the tampon expands sufficiently to substantially fill the vaginal cavity, menstrual fluid may flow along the tampon's side and bypass its absorbent portions such as the core.

Generally, tampons are manufactured from absorbent fibers, such as rayon, cotton, or a mixture of both fibers. The volume of absorbent fibers necessary to provide sufficient absorption capacity must be highly compressed to form a cylindrical tampon of sufficiently small size to allow for comfortable insertion into the body. The compression should be adequate to hold the tampon in the cylindrical shape until insertion. As a result the tampon, when first inserted into the body, is often highly compressed into a relatively non-conformable form with a relatively high initial density. Thus, the tampon is not able to immediately conform to the vaginal walls directly after insertion. The initial high density can also inhibit the rapid expansion of the tampon. Expansion, if it occurs at all, occurs only when the tampon comes into contact with a sufficient amount of menstrual fluids to swell the absorbent fibers and to release the expansion energy locked into the tampon when it is compressed. Thus, the tampon is susceptible to early bypass leakage as described above.

There have been several attempts to address the problem of early bypass leakage by providing rapidly expanding tampons. However, these designs suffer from two drawbacks: first, several designs are based upon synthetic materials which are not currently widely accepted for use in internal sanitary products, and second, many designs have insufficient stability and thus require the use of an applicator; they cannot be used as digital tampons. Designs based upon synthetic materials include those which use foams such as Schaefer, U.S. Pat. No. 3,815,601; Dulle, U.S. Pat. No. 3,794,029; and Fries et al., U.S. Pat. No. 4,341,214; or resilient fibers such as Wolfe et al., U.S. Pat. No. 4,543,098; and Gellert, U.S. Pat. No. 4,475,911. Designs which require applicators include Fries et al. and Gellert.

In addition, Walton et al., U.S. Pat. No. 4,627,849, describes the use of a pre-shortened batt made from natural fibers to obtain a more rapidly expanding compressed tampon. However, this design requires several additional manufacturing steps to form the pre-shortened batt.

There is a desire to avoid premature expansion of these compressed tampons, especially those using more resilient fibers. For example, Courtaulds PLC, EP 0 301 874 B1, discloses a tampon having multi-lobed regenerated cellulose fibers which patentee claims provide high absorbency and a cotton-like handle. These tampons are described as having good stability and absorbency. Longitudinally-expanding tampons having these fibers are described as having less expansion than conventional longitudinally-expanding tampons.

Therefore, what is needed is a radially-expanding tampon having substantial dimensional stability prior to use while rapidly expanding in high humidity environments.

SUMMARY OF THE INVENTION

We have developed a tampon which can expand in the presence of high humidity after insertion into a user's body to prevent early bypass leakage from occurring. This tampon is a substantially cylindrical mass of compressed fibers enclosed within a fluid-permeable cover. The tampon has a stability of at least about 15 N, and is capable of radially expanding upon exposure to a humid environment. The radius increases by at least about 10% after 15 minutes to 90% relative humidity at 40° C.

DETAILED DESCRIPTION OF THE INVENTION

Figure 1:
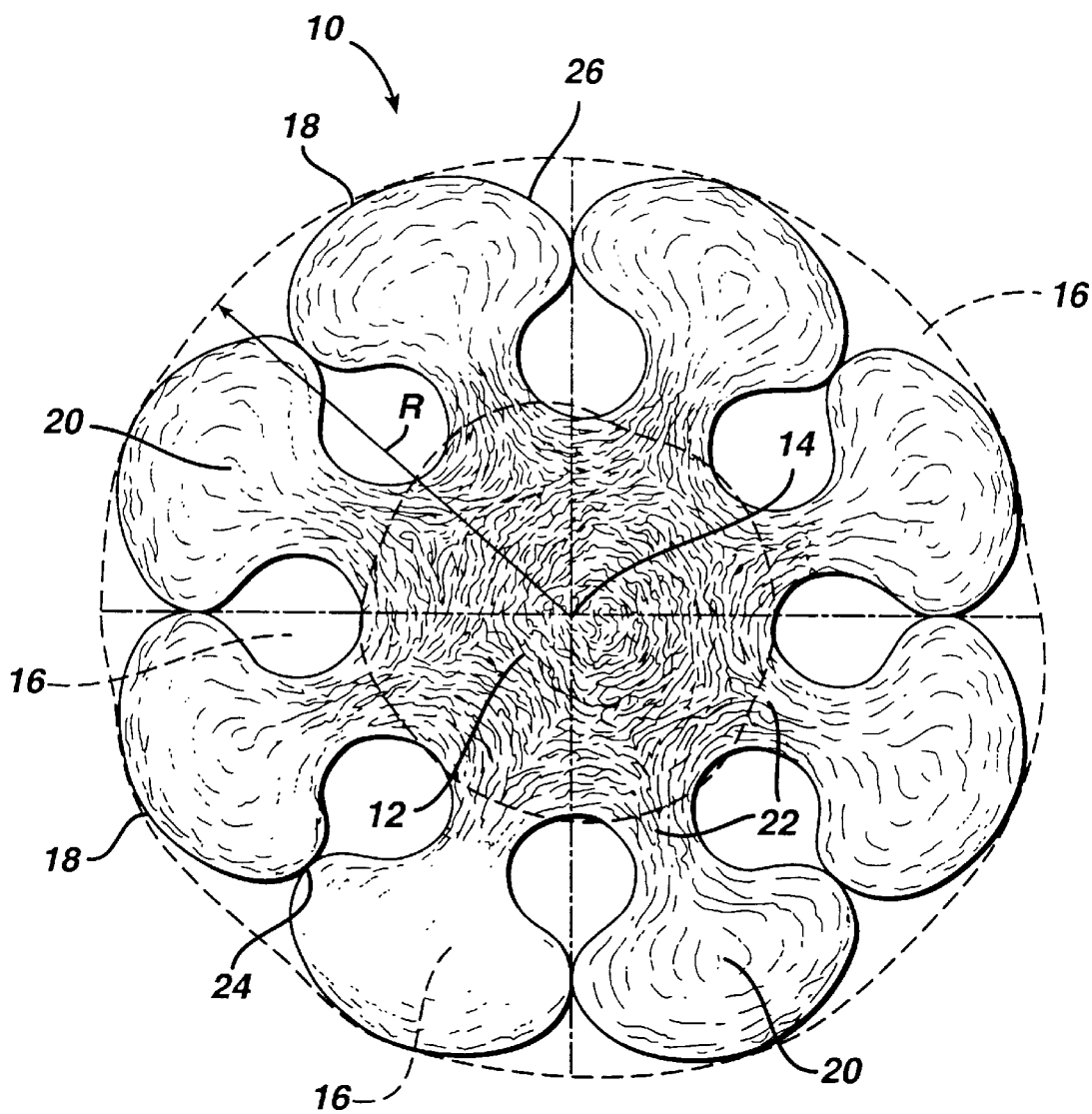
FIG. 1 is a cross-section of one embodiment of a tampon according to the present invention.

Absorbent tampons are generally cylindrical masses of compressed fibers having a substantially central axis and a radius which defines the outer circumferential surface of the tampon. Tampons are often formed by first obtaining a mass of nonwoven fibers called a tampon blank. This blank can be a rolled fibrous batt, a segment of a fibrous tow, a mass of randomly oriented fibers, a blank of substantially uniformly oriented fibers, and the like.

Thus, the fibers may have a number of orientations. Rolled blanks may be formed from a carded web which is then rolled about an axis either perpendicular or parallel to the major axis of the web. If the web is rolled about a perpendicular axis, a majority of the fibers are oriented in a circumferential manner or generally tangent to the tampon radius. If the web is rolled about a parallel axis, a majority of the fibers are oriented generally parallel to the central tampon axis. If the blank is formed of a fibrous tow, the majority of the fibers will generally be oriented parallel to the central tampon axis.

The tampon blank is relatively uncompressed and has a relatively low fiber density. It is often compressed to form a finished product having overall dimensions less than those of the blank. When pressure is released after moderate mechanical compression, a tampon tends to expand toward its original dimensions. Therefore, tampon blanks are generally over-compressed to allow them to rebound slightly to the desired density for use. Over-compression mechanically constricts expansion to prevent the tampon from expanding without added liquid.

The over-compression of the mass of fibers which form the tampon provides some degree of dimensional stability, especially longitudinal crush resistance. This measurement is generally described as the tampon's stability. Preferably, tampons of the present invention have a significant stability, at least about 15 N. More preferably, the tampons have a stability of at least about 20 N, and most preferably, they have a stability of about 30 N to about 85 N. Tampons with a stability which is too low do not have sufficient dimensional stability to maintain their basic structure during insertion as a digital tampon; tampons with a stability which is too high can be perceived as being too stiff or hard to be comfortably inserted as a digital tampon.

The stability of a tampon is measured using the crush test which measures, in Newtons (N), the longitudinal force required to buckle the tampon. The cylindrical tampon is placed with one end on fixed lower jaw of a test machine, the upper moveable jaw is brought down to contact the other end of the tampon and is then set to move down at a speed of 5 cm/mm. The force exerted by the tampon on the jaws of the test machine is measured continuously and the point at which this force begins to fall instead of rise is the point at which the tampon buckles. The maximum force achieved is the stability of the tampon. During the test the tampon is maintained in a controlled environment of 65% RH and 20° C.

Tampons are generally categorized in two classes: applicator tampons and digital tampons. Applicator tampons use a relatively rigid device to contain and protect the tampon prior to use. To insert the tampon into a body cavity, the applicator is partially inserted into the body cavity, and the tampon can be expelled therefrom. Because the tampon is protected by the rigid applicator device, the tampon need not have a high degree of dimensional stability. In contrast, digital tampons do not have an applicator to help guide them into the body cavity and require sufficient stability to allow insertion without using an applicator.

Compressed tampons may have a generally uniform fiber density throughout the tampon, or they may have regions of differing density as described in the commonly assigned applications to Friese et al., U.S. Ser. No. 07/596,454, and Leutwyler et al., U.S. Ser. No. 08/196,664, the disclosures of which are herein incorporated by reference. Preferably, the tampon 10 has a relatively dense core 12 substantially surrounding the central axis 14 and a less dense annulus 16 surrounding the core 12 and forming the outer circumferential surface 18. This is illustrated in FIG. 1. This density differential may be provided by relatively uniform fiber distribution within the core 12 and annulus 16, or it may be provided by a plurality of ribs 20 which extend radially (in the direction R) from the core 12. In a preferred embodiment, each rib 20 is separated from adjacent ribs where it is attached to the core 12, i.e., at its root 22, and each rib 20 contacts adjacent ribs, e.g., at 24, proximate the circumferential surface 18 of the tampon. In addition, the tampon has a cover 26.

The tampons fibers are compressible, that is, they can be compressed to hold a generally compressed form, but they also can expand to a relatively uncompressed state upon exposure to sufficient moisture. This moisture may be liquid or vapor. Preferably, the fibers include hydrophilic fibers, and more preferably, the fibers include absorbent fibers, i.e., individual fibers absorb fluid. A useful, non-limiting list of useful tampon fibers includes natural fibers such as cotton, wood pulp, jute, and the like; and processed fibers such as regenerated cellulose, cellulose nitrate, cellulose acetate, rayon, polyester, polyvinyl alcohol, polyolefin, polyamine, polyamide, polyacrylonitrile, and the like. Other fibers in addition to the above fibers may be included to add desirable characteristics to the absorbent body. For example, hydrophobic fibers may be used in outer surfaces of the tampon to reduce surface wetness and hydrophilic fibers may be used to increase the rate of fluid transport into and throughout the body. Preferably, the tampon fibers are rayon or cotton, and more preferably, the fibers are rayon. The fibers may have any useful cross-section.

Preferred fiber cross-sections include multi-limbed and non-limbed. More preferably, the fibers are predominantly multi-limbed. Multi-limbed, regenerated cellulosic fibers have been commercially available for a number of years. These fibers are known to possess increased specific absorbency over non-limbed fibers. One commercial example of these fibers is the Galaxy viscose rayon fibers available from Courtaulds PLC, London, England. These fibers are described in detail in Courtaulds PLC, EP 0 301 874 B1 (corresponding to U.S. Pat. Nos. 5,458,835; 5,634,914; and 6,333,108), the disclosure of which is hereby incorporated by reference. These multi-limbed fibers are described as comprising a solid filament of regenerated cellulosic material having a decitex of less than 5.0 and a multi-limbed cross-section, each limb having a length-to-width ratio of at least 2:1. The fibers are preferably staple length fibers having three or four limbs and a generally symmetrical cross-sectional shape, e.g., Y-, X, H, or T-shaped. A preferred cross-sectional shape is Y-shaped having an angle between limbs of about 120. Preferred regenerated cellulosic material are viscose having a cellulose content of 5 to 12 wt-% and a caustic soda content of 4 to 10 wt-%. The fibers are preferably spun having a salt figure of 4.0 to 12.0. It is expected that any multi-limbed commercial fiber or even other such fibers, not currently commercially available, would be useful in the practice of the present invention. It is merely required that the fibers lead to an absorbent body having a relatively high specific absorption capacity which is increased by the addition of a less absorbent, non-limbed fiber to form a fibrous absorbent body.

We have found that tampons including about 25 wt-% to about 100 wt-% of the multi-limbed fibers provide the early expansion properties of the present invention. The fibers may be a mixture of multi-limbed and non-limbed fibers. Preferably, the tampon includes about 25 wt-% to about 100 wt-% of the multi-limbed fibers and about 75 wt-% to about 0 wt-% of the non-limbed fibers. More preferably, the tampon includes about 50 wt-% to about 100 wt-% of the multi-limbed fibers and about 50 wt-% to about 0 wt-% of the non-limbed fibers.

Sufficient multi-limbed fibers are included into the tampon-forming fibrous web to provide a radial increases of at least about 10% after 15 minutes exposure to 90% relative humidity at 40° C. (90% RH @40° C.). More preferably, the tampon has a radial increase of at least about 20% after 15 minutes (90% RH @40° C.), and most preferably, the tampon has a radial increase of about 20% to about 25% after 15 minutes (90% RH @40° C.). The tampon preferably has a radial increase of at least about 15% after 30 minutes (90% RH @40° C.), and most preferably, the tampon has a radial increase of about 25% to about 40% after 30 minutes (90% RH @40° C.). The tampon preferably has a radial increase of at least about 15% after 45 minutes (90% RH @40° C.), and most preferably, the tampon has a radial increase of about 35% to about 50% after 45 minutes (90% RH @40° C.).

The non-limbed and multi-limbed fibers are preferably blended to a substantially uniform mixture of fibers. These fiber blending operations are known to those of ordinary skill in the art. For example, the fibers can be continuously metered into a saw-tooth opener. The blended fibers can be transported, e.g., by air through a conduit to a carding station to form a fibrous web. This web can be further processed to form a tampon. In a tampon forming process, the web can be formed into a narrow, fibrous sliver and spirally wound to form a tampon blank. In addition, a liquid-permeable cover material can be wrapped around the tampon blank to substantially contain the fibrous absorbent portion of the tampon.

During use, the tampons of the present invention absorb moisture and liquids and radially expand. As used in the specification and claims, the term "radially expand" and variations of this term relate to the expansion of generally cylindrical tampons. These tampons expand primarily in a direction perpendicular to the central axis of the tampon. Preferably, the tampons expand in at least one direction perpendicular to the central axis, more preferably, at least two directions. Most preferably, the tampons expand substantially uniformly in all directions perpendicular to the central axis.

The tampon blank is substantially enclosed by a fluid-permeable cover. Thus, the cover encloses a majority of the outer surface of the tampon. This may be achieved as disclosed in Friese, U.S. Pat. No. 4,816,100, the disclosure of which is herein incorporated by reference. In addition, either or both ends of the tampon may be enclosed by the cover. Of course, for processing or other reasons, some portions of the surface of the tampon may be free of the cover. For example, the insertion end of the tampon and a portion of the cylindrical surface adjacent this end may be exposed, without the cover to allow the tampon to more readily accept fluids.

The cover can ease the insertion of the tampon into the body cavity and can reduce the possibility of fibers being separated from the tampon. Useful covers are known to those of ordinary skill in the art. They may be selected from an outer layer of fibers which are fused together (such as by thermobonding), a nonwoven fabric, an apertured film, or the like. Preferably, the cover has a hydrophobic finish.

EXAMPLES

Example 1

A series of fibrous webs were formed by adding a measured amount of multi-limbed regenerated cellulosic staple fibers (Galaxy fibers, 3.3 denier, rayon fibers, available from Courtaulds Fibres, London, England) and non-limbed regenerated cellulosic staple fibers (Danufil™ fibers, 3.6 denier, rayon fibers, available from Hoescht Kehlheim, Kehlheim, Germany). The fiber components were weighed using a component scale, mixed together in a bale breaker and subsequently opened in a saw-tooth opener. The resulting blend was carded to obtain the fibrous web. These webs were then used to manufacture compressed, radially-expanding, generally cylindrical tampons according to the process of the commonly assigned, applications to Friese et al., U.S. Ser. No. 07/596,454, and Leutwyler et al., U.S. Ser. No. 08/196, 664, and covered according to the process of Friese, U.S. Pat. No. 4,816,100. These tampons were conditioned at 65% RH @21° C. for at least 24 hours and the initial diameter was measured. The composition and initial diameter of these tampons are identified below in Table 1. The standard deviations of the diameter are included in parenthesis.

TABLE 1

| Test Product | Sample Size (n) | Avg. Diameter (mm) | Wt-% Galaxy (%) | Wt-% Rayon (%) |
|---|---|---|---|---|
| Comp. Ex. A | 5 | 13.20 (0.17) | 0 | 100 |
| Ex. B | 5 | 13.50 (0.17) | 100 | 0 |
| Ex. C | 5 | 13.46 (0.13) | 75 | 25 |
| Ex. D | 5 | 13.38 (0.12) | 50 | 50 |
| Ex. E | 5 | 13.20 (0.14) | 25 | 75 |

The conditioned tampons were then placed into a high humidity environment (90% relative humidity at 40° C.). During this exposure, the tampon diameter was measured at 15 minute intervals. The results are illustrated below in Table 2. Again, the standard deviations of the diameter measurements are included in parenthesis.

TABLE 2

| | Diameter at: | | | |
|---|---|---|---|---|
| Test Product | 15 Min. (mm) | 30 Min. (mm) | 45 Min. (mm) | 60 Min. (mm) |
| Comp. Ex. A | 13.83 (0.66) | 14.30 (0.27) | 14.52 (0.37) | 15.09 (0.24) |
| Ex. B | 16.83 (0.73) | 18.15 (1.00) | 19.36 (0.85) | 20.06 (0.63) |
| Ex. C | 16.06 (0.27) | 17.40 (0.69) | 18.79 (0.39) | 19.91 (0.39) |
| Ex. D | 15.97 (0.54) | 17.42 (0.50) | 18.60 (0.48) | 19.76 (0.30) |
| Ex. E | 14.45 (0.22) | 14.97 (0.47) | 15.19 (0.34) | 15.10 (0.32) |

From these data, it can be seen that the incorporation of multi-limbed rayon fibers increases the early expansion of a compressed tampon in a high humidity environment over a compressed tampon which does not include such fibers. It should be noted that the tampons do not take up a significant amount of fluid during this experiment (approx. 0.1 g/tampon after 60 min.).

Example 2

A series of fibrous webs having 75 wt-% Galaxy™ fibers and 25 wt-% Danufil™ fibers were formed as in Example 1 above. The fibrous webs were then formed into tampon blanks and compressed. Three different tampon blank styles were formed: folded, rolled, and cut. To form the folded blank, a section of about eight times the length of the tampon blank was folded back and forth at five fold lines, perpendicular to the length of the web. Each fold line was separated by the length of the tampon blank. Thus, the tampon blank had two raw cut edges and two fold lines at one longitudinal edge thereof and three fold lines at the opposite longitudinal edge, and a major portion of the fibers was oriented substantially parallel to the central axis. To form the rolled blank, a section of fibrous web was wound about a central axis. Thus, a major portion of the fibers was oriented substantially circumferentially. To form the cut blank, the intermediate fold lines of the folded blank were replaced by cut lines. Thus, the tampon blank had six raw cut edges at each longitudinal end thereof, and a major portion of the fibers was oriented substantially parallel to the central axis. These tampon blanks were further processed to form tampons and conditioned as described above. The composition and initial diameter of these tampons are identified below in Table 3. The standard deviations of the diameter are included in parenthesis.

TABLE 3

| Test Product | Sample Size (n) | Avg. Diameter (mm) | Tampon Blank Type |
|---|---|---|---|
| Ex. F | 6 | 13.24 (0.26) | Folded |
| Ex. G | 6 | 13.12 (0.13) | Rolled |
| Ex. H | 6 | 13.25 (0.10) | Cut |

Again, the conditioned tampons were placed into a high humidity environment (90% relative humidity at 40° C.). During this exposure, the tampon diameter was measured at 15 minute intervals. The results are illustrated below in Table 4. Again, the standard deviations of the diameter measurements are included in parenthesis.

TABLE 4

| Test Product | Diameter at: | | | |
|---|---|---|---|---|
| | 15 Min. (mm) | 30 Min. (mm) | 45 Min. (mm) | 60 Min. (mm) |
| Ex. F | 14.76 (0.88) | 15.81 (0.96) | 16.27 (1.00) | 16.57 (1.04) |
| Ex. G | 15.32 (0.18) | 16.18 (0.44) | 16.43 (0.28) | 16.84 (0.38) |
| Ex. H | 15.54 (0.29) | 16.31 (0.75) | 16.60 (0.14) | 16.93 (0.19) |

From these data, it can be seen that the compressed tampons of the present invention exhibit the early expansion in a high humidity environment whether the fibers are oriented circumferentially or longitudinally.

The specification and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of forming a compressed, radially-expanding, generally cylindrical tampon having improved early expansion characteristics comprising the steps of:

forming a web having about 25 to 100 wt-% of resilient staple fibers having a multi-limbed cross-section having at least three limbs and about 0 to 75 wt-% of non-limbed staple fibers, said web having a length dimension, substantially perpendicular to both a width dimension and a thickness dimension;

orienting a majority of said multi-limbed fibers substantially parallel to said length dimension;

winding a portion of said web about an axis substantially parallel to said width dimension to form a generally cylindrical tampon blank having a central axis, said tampon blank having a length substantially corresponding to the width dimension of said web;

substantially enclosing said tampon blank with a fluid-permeable cover; and compressing said tampon blank radially inward toward said central axis.

2. The method of claim 1 wherein the step of compressing the tampon blank comprises forming a fibrous core substantially surrounding the central axis, the core having a first average density, and a plurality of ribs which extend radially from the core, wherein each rib is separated from adjacent ribs where it is attached to the core and each rib contacts adjacent ribs proximate the circumferential surface of the tampon.

3. A method of increasing early expansion of a compressed, radially-expanding, generally cylindrical tampon comprising the steps of:

incorporating an effective amount of resilient staple fibers to provide an increase in compressed tampon diameter by at least about 10% after 15 minutes exposure to about 90% relative humidity at about 40° C. into a web having a length dimension, substantially perpendicular to both a width dimension and a thickness dimension, said resilient staple fibers having a multi-limbed cross-section having at least three limbs;

orienting a majority of said multi-limbed fibers substantially parallel to said length dimension of said web;

winding said web about an axis substantially parallel to said length dimension to form a substantially continuous, low density cylinder of fibers having a central axis;

substantially enclosing said web with a fluid-permeable cover;

compressing said cylinder of fibers radially inward toward said central axis to form a compressed cylinder; and severing a length of said compressed cylinder to form a tampon.

4. The method of claim 3 wherein the step of compressing the tampon blank comprises forming a fibrous core substantially surrounding the central axis, the core having a first average density, and a plurality of ribs which extend radially from the core, wherein each rib is separated from adjacent ribs where it is attached to the core and each rib contacts adjacent ribs proximate the circumferential surface of the tampon.

* * * * *